United States Patent [19]

Buchecker et al.

[11] Patent Number: 5,498,367
[45] Date of Patent: Mar. 12, 1996

[54] OPTICALLY ACTIVE TOLANES

[75] Inventors: Richard Buchecker, Zurich, Switzerland; Guy Marck, Lutterbach, France; Martin Schadt, Seltisberg, Switzerland

[73] Assignee: Hoffmann-La Roche Inc., Nutley, N.J.

[21] Appl. No.: 390,609

[22] Filed: Feb. 17, 1995

[30] Foreign Application Priority Data

Mar. 30, 1994 [CH] Switzerland ............... 952/94

[51] Int. Cl.$^6$ .................. C09K 19/34; C09K 49/30; C07B 317/10
[52] U.S. Cl. .................. 252/299.61; 252/299.01; 252/299.63; 547/430
[58] Field of Search .................. 252/299.61, 299.63, 252/299.66; 549/429, 430

[56] References Cited

U.S. PATENT DOCUMENTS

| | | | |
|---|---|---|---|
| 4,966,726 | 10/1990 | Scherowsky et al. | 252/299.6 |
| 5,328,637 | 7/1994 | Buchecker et al. | 252/299.61 |
| 5,360,577 | 11/1994 | Buchecker et al. | 252/299.61 |

FOREIGN PATENT DOCUMENTS

| | | |
|---|---|---|
| 234437 | 2/1987 | European Pat. Off. |
| 441213 | 8/1991 | European Pat. Off. |
| 501268 | 2/1992 | European Pat. Off. |
| 0593997 | 10/1993 | European Pat. Off. |

OTHER PUBLICATIONS

M. Schadt, Liquid Crystals vol. 14, pp. 73–104 (1993).

*Primary Examiner*—Shean C. Wu
*Attorney, Agent, or Firm*—George M. Gould; George W. Johnston; Robert A. Silverman

[57] ABSTRACT

A chiral dopant of the formula

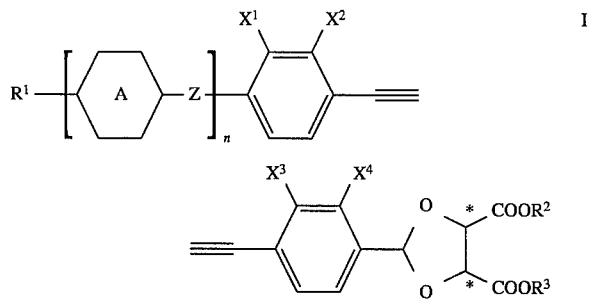

wherein ring A is 1,4-phenylene which is optionally substituted with one or more fluorine atoms, chlorine atoms, bromine atoms, cyano groups, or methyl groups, and in which one or two CH groups can be replaced by nitrogen, or is trans-1,4-cyclohexylene;

Z is a single covalent bond, —$CH_2CH_2$—, —$CH_2O$— or —$OCH_2$—;

$X^1, X^2, X^3, X^4$ each independently are hydrogen or fluorine;

$R^1$ is hydrogen, is alkyl with 1 to 12 carbon atoms which is optionally substituted with one or more fluorine or chlorine atoms and in which one or two non-adjacent $CH_2$ groups can be replaced by —O—, is alkenyl with 2 to 12 carbon atoms, which is optionally substituted with one or more fluorine or chlorine atoms and in which one or two non-adjacent $CH_2$ groups can be replaced by —O—, is a group of the formula

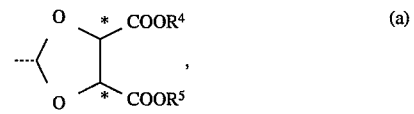

and when $R^1$ is bonded to an aromatic ring, can also be fluorine, chlorine, cyano, $CF_3$, $OCHF_2$ or —$OCF_3$;

$R^2, R^3, R^4, R^5$ are alkyl with 1 to 8 carbon atoms or alkenyl with 2 to 8 carbon atoms;

n is 0 or 1; and

* is a center of chirality.

8 Claims, No Drawings

OPTICALLY ACTIVE TOLANES

BACKGROUND OF THE INVENTION

1. Field

The invention relates to chiral dopants for liquid crystals and liquid crystalline mixtures which contain such dopants and their use for optical and electro-optical devices.

2. Background

Liquid crystal materials for cholesteric filters frequently contain, in addition to nematic liquid crystals, one or more optically active additives for the induction of a chiral structure. For example, for the use of such liquid crystals in optical filters a nematic liquid crystal is doped with optically active additives such that on the one hand a fixed rotational direction of the helix results and on the other hand the desired helical pitch is induced. In addition to the chiral properties of dopants, certain dielectric and optical properties are also desirable for optimal application in cholesteric filters. In order to achieve a bandwidth of the selective filter reflection which is as great as possible, chiral dopants having a large optical anisotropy are, for example, required. Further, cholesteric filters can be built with dopants of negative dielectric anisotropy which give rise to a planar orientation without disinclinations in electric fields. A high optical quality of the filter can thus be realized [M. Schadt, Liquid Crystals 14, 73 (1993)].

Cholesteric liquid crystals reflect selective light in a wavelength range for which the wavelength is about the same as the helical pitch. The spectral width of this reflection light can be varied by suitable choice of the liquid crystal. The reflected light is completely circularly polarized. The rotational direction of the reflected light depends on the direction of rotation of the cholesteric helical structure. The opposite circularly polarized light is transmitted unimpaired. These properties can be used for the production of optical filters, polarizers, analyzers etc.

Cholesteric liquid crystals for the above applications can preferably consist of a nematic or cholesteric basic material and one or more chiral dopants, which permits a simple adjustment of the desired helical pitch.

In order to achieve cholesteric mixtures having a pitch in the range of the wavelength of visible light, the chiral dopants should have a twisting capacity which is as high as possible and should have a good solubility in usual liquid crystal materials. Furthermore, the chiral dopants should have an adequate stability, should have a good compatibility with the mesophase type of the liquid crystal material and should not restrict the mesophase range too severely. Such properties would also be desirable for chiral dopants in order to produce the highly twisted nematic structures referred to earlier, as their amount can be kept low in order that the properties of the liquid crystal material are influenced only immaterially.

SUMMARY OF THE INVENTION

The invention relates to an optically active compound of the formula $$R^1-\left[\left(A\right)-Z\right]_n-\text{(aryl with }X^1, X^2\text{)}-\equiv\quad \text{I}$$

-continued $$\equiv-\text{(aryl with }X^3, X^4\text{)}-\underset{O}{\overset{O}{\diagdown}}\overset{*}{\diagup}\underset{COOR^3}{\overset{COOR^2}{\diagup}}$$

wherein
- ring A is 1,4-phenylene, which is unsubstituted or mono- or multiply-substituted and in which optionally one or two CH groups can be replaced by nitrogen, or trans-1,4-cyclohexylene;
- Z is a single covalent bond, —CH$_2$CH$_2$—, —CH$_2$O— or —OCH$_2$—;
- X$^1$,X$^2$,X$^3$,X$^4$ each independently are hydrogen or fluorine;
- R$^1$ is hydrogen, alkyl or alkenyl with 1 or, respectively, 2 to 12 carbon atoms, which is unsubstituted or mono- or multiply-substituted with fluorine or chlorine and in which one or two non-adjacent CH$_2$ groups can be replaced by —O—, or a group of the formula $$\underset{O}{\overset{O}{\diagdown}}\overset{*}{\diagup}\underset{COOR^5}{\overset{COOR^4}{\diagup}} \quad (a)$$

or when R$^1$ is bonded to an aromatic ring also fluorine, chlorine, cyano, CF$_3$, OCHF$_2$ or —OCF$_3$;
- R$^2$,R$^3$,R$^4$,R$^5$ are alkyl or alkenyl with 1 or, respectively, 2 to 8 carbon atoms;
- n is 0 or 1; and
- * is a center of chirality.

DETAILED DESCRIPTION OF THE INVENTION

An optically active compound of the formula:

$$R^1-\left[\left(A\right)-Z\right]_n-\text{(aryl with }X^1, X^2\text{)}-\equiv\quad \text{I}$$

$$\equiv-\text{(aryl with }X^3, X^4\text{)}-\underset{O}{\overset{O}{\diagdown}}\overset{*}{\diagup}\underset{COOR^3}{\overset{COOR^2}{\diagup}}$$

wherein
- ring A is 1,4-phenylene which is optionally substituted with one or more fluorine atoms, chlorine atoms, bromine atoms, cyano groups, or methyl groups, and in which one or two CH groups can be replaced by nitrogen, or is trans-1,4-cyclohexylene;
- Z is a single covalent bond, —CH$_2$CH$_2$—, —CH$_2$O— or —OCH$_2$—;
- X$^1$,X$^2$,X$^3$,X$^4$ each independently are hydrogen or fluorine;
- R$^1$ is hydrogen, is alkyl with 1 to 12 carbon atoms which is optionally substituted with one or more fluorine or chlorine atoms and in which one or two non-adjacent CH$_2$ groups can be replaced by —O—; is alkenyl with 2 to 12 carbon atoms which is optionally substituted with one or more fluorine or chlorine atoms and in which one or two non-adjacent CH$_2$ groups can be replaced by —O—, is a group of the formula

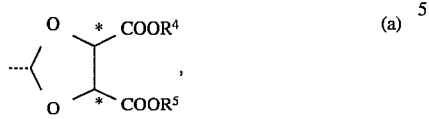

and when R$^1$ is bonded to an aromatic ring, can also be fluorine, chlorine, cyano, CF$_3$, OCHF$_2$ or —OCF$_3$;

R$^2$,R$^3$,R$^4$,R$^5$ are alkyl with 1 to 8 carbon atoms or alkenyl with 2 to 8 carbon atoms;

n is 0 or 1; and

* is a center of chirality.

The compounds of formula I accordingly have at least one optically active dioxolane ring. The dioxolane set forth in formula I has a chiral carbon atom in positions 4 and 5 (i.e. adjacent to the residues —COOR$^2$ and —COOR$^3$). In order to achieve optical activity the carbon atom in position 4 of the dioxolane ring must be present wholly or predominantly in the R or S form and, where R$^2$ and R$^3$ are identical, the carbon atom in position 5 of the dioxolane ring should have wholly or predominantly the same configuration as the carbon atom in position 4 or an R/S ratio of 50:50. In order to achieve a twisting capacity which is as high as possible, the carbon atom in position 4 of the dioxolane ring should preferably be present in the optically most possible pure form in the R or S configuration and the carbon atom in position 5 of the dioxolane ring should be present in the optically most possible pure form in either configuration, which intensifies the twisting capacity. The (4R,5R) isomers and the (4S,5S) isomers of the compounds of formula I are preferred optical isomers having a high twisting capacity.

The compounds of formula I have a very good solubility in usual liquid crystal materials and permit a very high twisting of the liquid crystal structure. In contrast to known materials having a high twisting capacity, the clearing points of liquid crystals are, as a rule, not lowered or lowered only insignificantly upon the addition of compounds of formula I. Many of the compounds in accordance with the invention even themselves have liquid crystalline properties. The compounds of formula I can be manufactured readily, have a relatively low viscosity and an adequate stability towards electric and magnetic fields. They therefore fulfill the requirements referred to above in an optimal manner.

The properties of the compounds of formula I can be varied depending on the choice and the significance of ring A and the substituents R$^1$, R$^2$, R$^3$, X$^1$, X$^2$, X$^3$ and X$^4$. For example, an additional aromatic ring leads to higher values of the optical anisotropy. Polar end groups R$^1$, such as cyano, halogen, trifluoromethyl or trifluoromethoxy, or a ring, such as pyrimidine-2,5-diyl, increase, for example, the dielectric anisotropy. Lateral halogen substituents contribute to the dielectric constant not only parallel to, but also perpendicular to the longitudinal axis of the molecule, which can be used, depending on the substitution pattern, to increase or reduce the dielectric anisotropy or to produce a negative dielectric anisotropy. Further, a possible tendency to form highly ordered smectic phases can be largely suppressed for the most part and often the solubility can also be improved by lateral substituents on one or more rings. Furthermore, the elastic properties, the threshold potentials, the response times, the mesophases etc. can be modified by a C=C double bond in the side-chain.

The present invention therefore permits, in addition to the induction of a high twisting, additionally the optimization of liquid crystalline, optical and electro-optical properties in a wide range according to application and desired properties.

The term "1,4-phenylene which is optionally substituted with one or more fluorine atoms, chlorine atoms, bromine atoms, cyano groups, or methyl groups, and in which 1 or 2 CH groups can be replaced by nitrogen," embraces groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano-1,4-phenylene, 2-methyl-1,4-phenylene, pyridine-2,5-diyl, pyrazine-2,5-diyl, pyrimidine 2,5-diyl and the like. 1,4-Phenylene, 2-fluoro-1,4-phenylene, 2,3-difluoro-1,4-phenylene, pyridine-2,5-diyl, pyrimidine-2,5-diyl and the like are preferred groups.

The terms "alkyl with 1 to 12 carbon atoms which is optionally substituted with one or more fluorine or chlorine atoms and in which one or two non-adjacent CH$_2$ groups can be replaced by —O—," and "alkenyl with 2 to 12 carbon atoms which is optionally substituted with one or more fluorine or chlorine atoms and in which one or two non-adjacent CH$_2$ groups can be replaced by —O—" embraces in the scope of the present invention straight-chain and branched (optionally chiral) residues such as alkyl, 1E-alkenyl, 3E-alkenyl, 4-alkenyl, alkenyl having a terminal double bond, alkoxy, 2E-alkenyloxy, 3-alkenyloxy, alkenyloxy having a terminal double bond, alkoxyalkyl, alkenyloxyalkyl, 1-fluoroalkyl, 2-fluoroalkyl, 2-fluoroalkoxy, 1-chloroalkyl, 2-chloroalkyl, 2-chloroalkoxy, 1-methylalkyl, 2-methylalkyl, 1-methylalkoxy, 2-methylalkoxy and the like. Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1E-propenyl, 1E-butenyl, 1E-pentenyl, 1E-hexanyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, -nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methylheptyloxy, 2-methylbutyloxy, 3-methylpentyloxy, allyloxy, E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, allyloxymethyl, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, 2-chloropropyloxy, chlorobutyloxy and the like.

"Alkyl" in the residues R$^2$, R$^3$, R$^4$ and R$^5$ is a straight-chain or branched, optionally chiral group, with 1 to 12 carbon atoms, such as methyl, ethyl, propyl, isopropyl, butyl, isobutyl, 2-butyl (=1methylpropyl), 2-methylbutyl, pentyl, hexyl, heptyl, octyl, 2-octyl (=1-methylheptyl), and the like. Preferred alkyl residues in R$^2$, R$^3$, R$^4$ and R$^5$ and as a substituent to ring A are C$_1$–C$_5$-alkyl residues, especially methyl, ethyl, n-propyl, n-butyl and n-pentyl.

Preferred compounds of formula I are those in which n=1. Further, those compounds of formula I in which X$^1$ and X$^2$ or X$^3$ and X$^4$ are fluorine are preferred. In the case of particularly preferred compounds of formula I R$^1$ is alkyl or alkoxy with 1 to 6 carbon atoms or is alkenyl, alkenyloxy or alkoxyalkyl with 2 to 6 carbon atoms, or is alkoxyalkenyl with 3 to 6 carbon atoms.

In particular, those compounds of formula I in which R$^1$ is a group of the formula

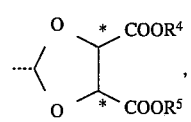
and n=0 or 1 are preferred.
(a) Especially preferred compounds of formula I are therefore optically active compounds of the following formulae
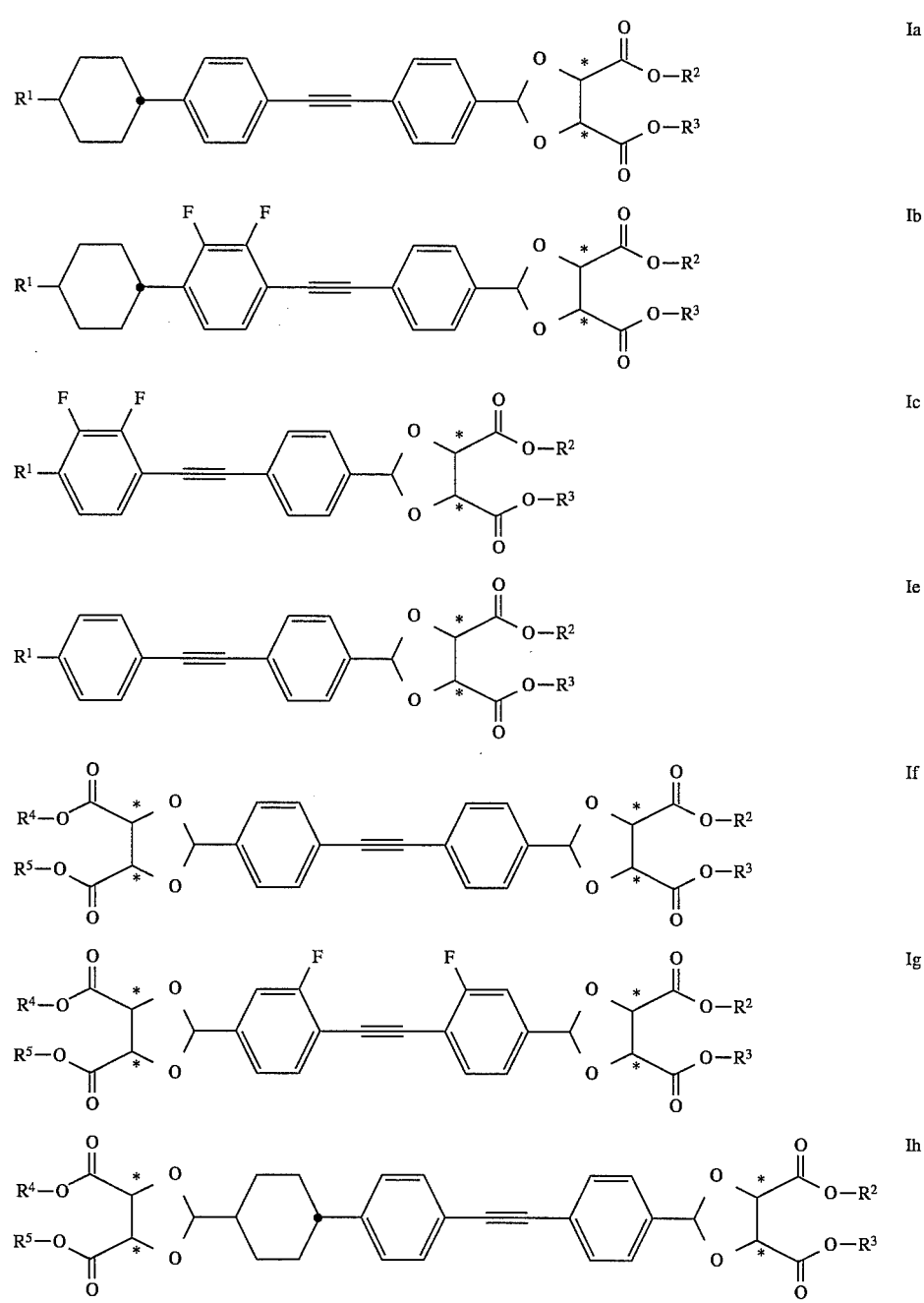
and

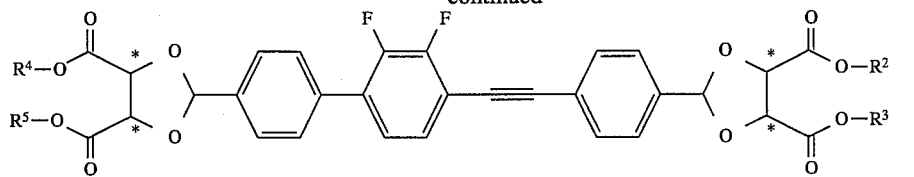

wherein $R^1$ is hydrogen, alkyl with 1 to 12 carbon atoms which is optionally substituted with one or more fluorine or chlorine atoms and in which one —$CH_2$-group can be replaced by —O—, is alkenyl with 2 to 12 carbon atoms which is optionally substituted with one or more fluorine or chlorine atoms and in which one —$CH_2$— group can be replaced by —O—, and when $R^1$ is bonded to an aromatic ring, can also be fluorine, chlorine, cyano, —$CF_3$, —$OCHF_2$ or $OCF_3$. $R^2$, $R^3$, $R^4$ and $R^5$ are as previously defined.

Of the compounds of formulae If to Ii there are preferred those in which $R^2$ is the same as $R^4$ and $R^3$ is the same as $R^5$. Those compounds of formulae If to Ii in which $R^2$ and $R^3$ are the same as $R^4$ and $R^5$ are particularly preferred.

The compounds in accordance with the invention can be manufactured readily in a known manner. Acetylene couplings, as generally used for the manufacture of tolanes, are especially suitable. Thus, for example, a phenylacetylene derivative 3 can be coupled with an optically active phenyldioxolane 2, which carries in the paraposition a suitable substituent such as, for example, iodine, bromine or trifluoromethylsulphonate (OTf) as the leaving group, with the aid of a suitable palladium catalyst (Scheme 1).

different from $R^2$ and $R^3$ can also be manufactured in this manner. The method is illustrated in more detail in Scheme 2.

Scheme 1

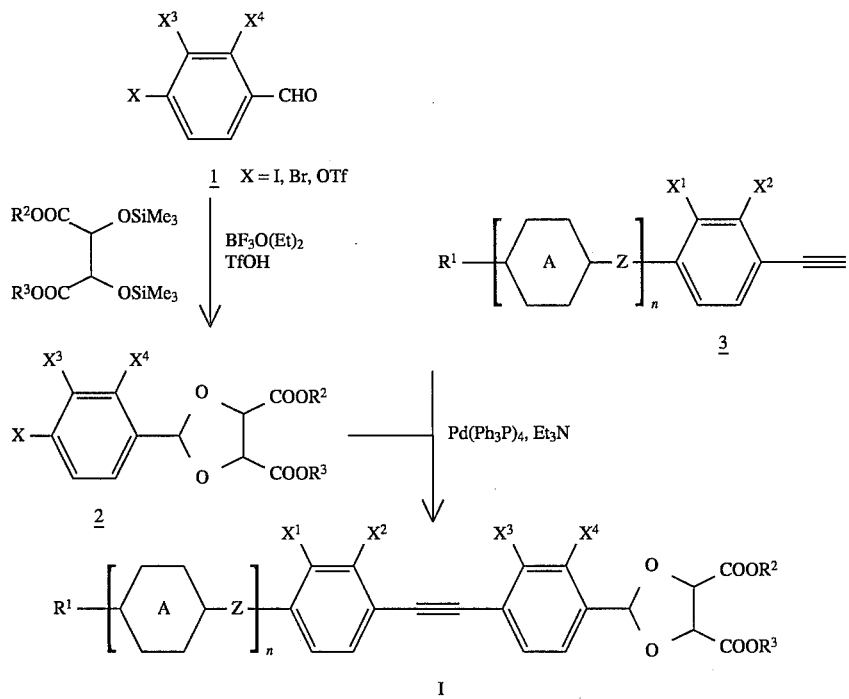

This method is especially suitable for the manufacture of compounds of formulae Ia to Ie. Compounds of formula I in which $R^1$ is a dioxolane ring and in which $R^4$ and $R^5$ are

Scheme 2
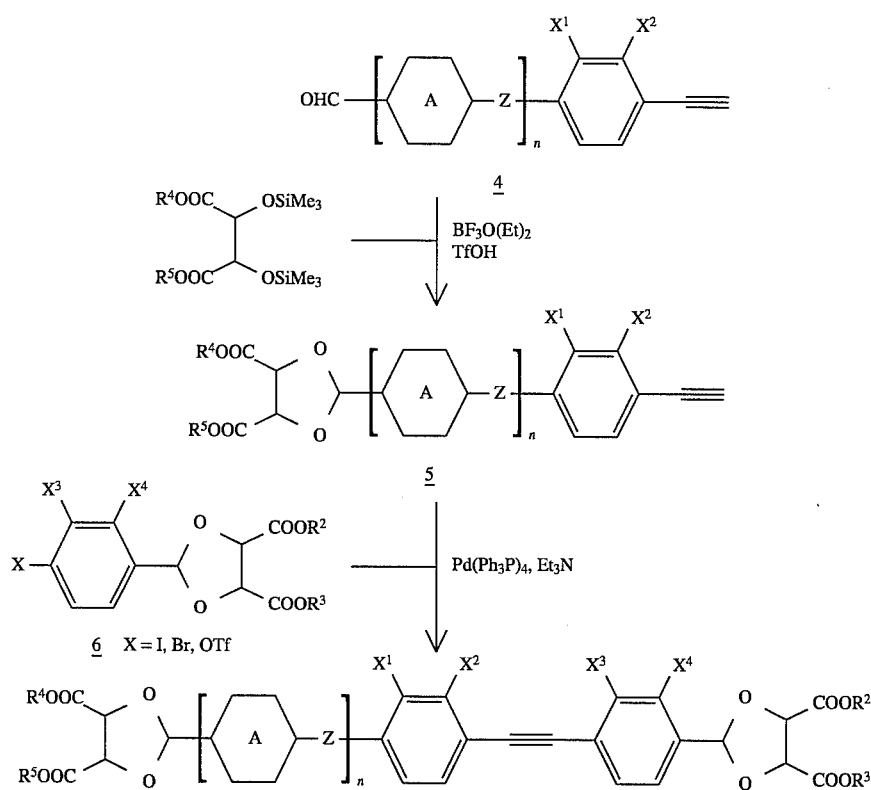
Compounds of formulae Ia to Ie, or compounds of formulae If to Ii in which $R^2$ is the same as $R^4$ and $R^3$ is the same as $R^5$, can conveniently be manufactured as shown in Scheme 3. In this, the dioxolane ring or both dioxolane rings are formed at the end of the synthesis by acetalization of a mono- or dialdehyde with the desired tartaric acid diester.
Scheme 3
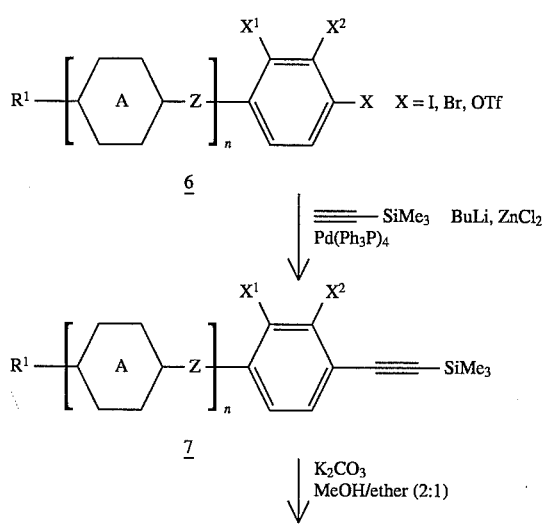

-continued
Scheme 3

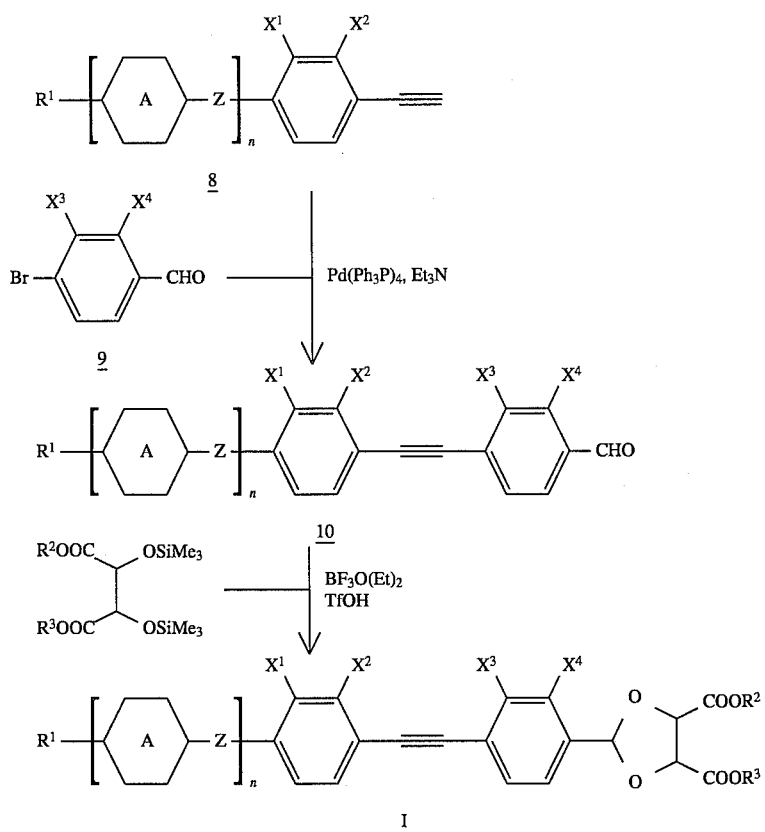

The acetylene derivatives set forth as starting materials in Schemes 1 and 2 are known or are analogues of known compounds. Their preparation has been described repeatedly in the literature, for example in EP-A 501268 or EP-A No. 0593997. Moreover, they can be prepared in accordance with Scheme 3 in a known manner by coupling with trimethylsilylacetylene and subsequent hydrolysis.

The formation of the dioxolane ring takes place by acetalizing the aldehyde starting material with a suitable tartaric acid diester, preferably in silylated form. Analogous reactions are described, for example, in THL 21, 1357 (1980).

In the case of aldehydes which have sufficient stability, the acetalization to the dioxolane can also be carried out using boron trifluoride etherate.

The invention is also concerned with liquid crystalline mixtures containing a liquid crystalline carrier material and one or more optically active compounds of formula I. Suitable carrier materials are basically all liquid crystal materials which have a twistable liquid crystal phase with an adequate mesophase range. The compounds of formula I are especially suitable as chiral dopants for nematic or cholesteric carrier materials. The liquid crystalline carrier material can be a single compound or a mixture and preferably has a clearing point of at least about 60° C.

The content of chiral dopant of formula I is determined essentially by its twisting capacity and the desired pitch. The content of chiral dopant can therefore vary in a wide range depending on the application and can be, for example, about 0.1–30 wt. %. For indicating devices based on liquid crystals having a twisted nematic structure a pitch of about 3–40 mm is mainly required depending on the type of cell and thickness of cell and therefore a correspondingly smaller amount is sufficient. On the other hand, for applications which are based on the reflection of visible light by cholesteric layers, pitches of less than 2 mm, for example about 0.4–0.6 mm, are necessary, which requires a correspondingly higher content of chiral dopant.

Suitable liquid crystalline carrier materials are known in large numbers and are commercially available. As a rule, liquid crystalline mixtures containing 2 or more components as carrier materials are preferred. Basically, however, one liquid crystalline compound can also be used as the carrier material when it has a sufficiently broad mesophase.

The mixtures in accordance with the invention preferably contain, in addition to one or more compounds of formula I, one or more compounds from the group of compounds of the general formulae

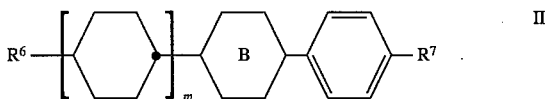

II

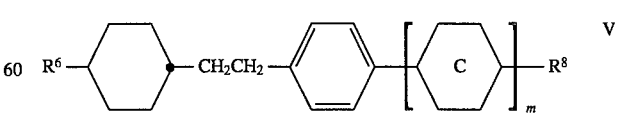

V

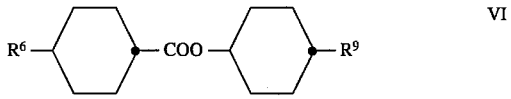

VI

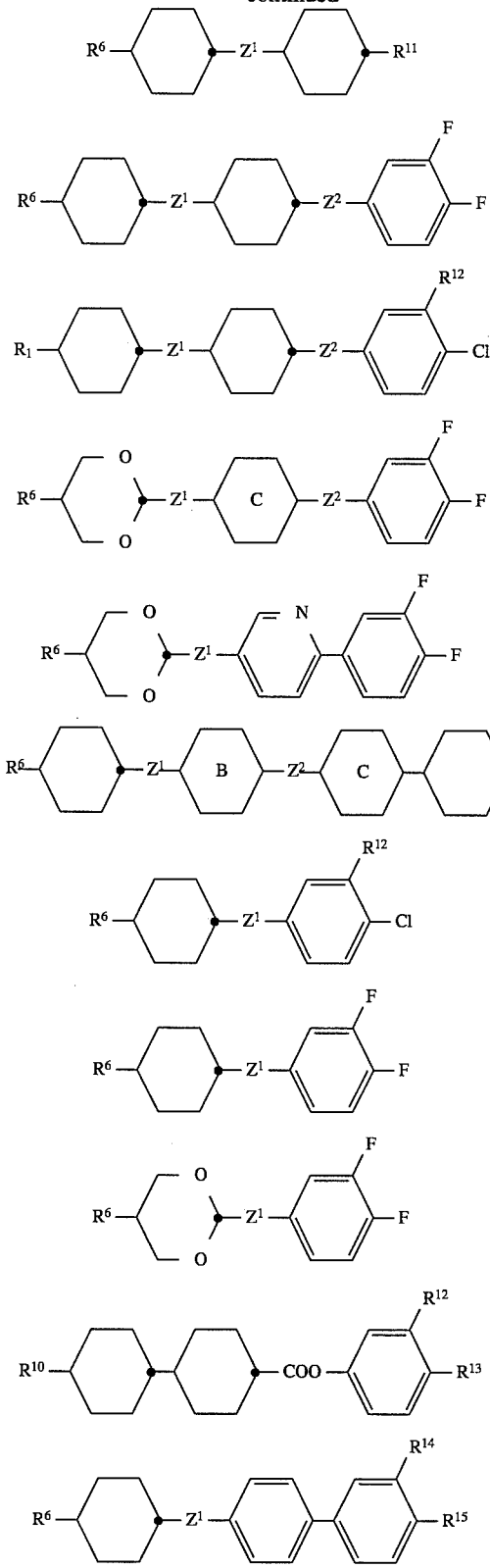

wherein

R⁶,R⁹ is alkyl, alkoxyalkyl, 3E-alkenyl, 4-alkenyl or on saturated rings also 1E-alkenyl;

m is 0 or 1;

ring B is 1,4-phenylene, pyridine-2,5-diyl, pyrimidine-2,5-diyl, trans-1,4-cyclohexylene or trans-1,3-dioxane-2,5-diyl;

R⁷ is cyano, isothiocyanato, fluorine, alkyl, 3E-akenyl, 4-alkenyl, alkoxy, 2E-alkenyloxy, 3-alkenyloxy or 1-alkynyl;

ring C is 1,4-phenylene or trans- 1,4-cyclohexylene;

R⁸ is alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

R¹⁰ is alkyl, 1E-alkenyl, 3E-alkenyl or 4-alkenyl;

R¹¹ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

Z¹,Z² each independently are a single covalent bond or —CH₂CH₂—, with two aromatic rings always being linked by a single covalent bond;

R¹² is hydrogen, fluorine or chlorine;

R¹³ is cyano, fluorine or chlorine;

R¹⁴ is hydrogen or fluorine; and

R¹⁵ is fluorine or chlorine.

The above term "saturated ring" embraces trans-1,4-cyclohexylene and trans-1,3-dioxane-2,5-diyl. Each of the residues R⁶ to R¹¹ preferably has 1 or, respectively, 2 to 12 carbon atoms, especially 1 or, respectively, 2 to 7 carbon atoms. Straight-chain residues are generally preferred.

The term "alkyl" preferably denotes in this connection straight-chain residues with 1 to 12 carbon atoms, preferably with 1 to 7 carbon atoms, such as, for example, methyl, ethyl, propyl, butyl, pentyl, hexyl or heptyl.

The term "alkoxyalkyl" preferably denotes in this connection straight-chain residues with 1 to 12 carbon atoms, especially with 1 to 7 carbon atoms, such as, for example, methoxymethyl, ethoxymethyl, propyloxymethyl, butyloxymethyl, methoxypropyl and the like.

The term "alkoxy" preferably denotes in this connection straight-chain residues with 1 to 12 carbon atoms, especially with 1 to 7 carbon atoms, such as, for example, methoxy, ethoxy, propyloxy, butyloxy, pentyloxy, hexyloxy, heptyloxy and the like.

The term "1E-alkenyl" preferably denotes in this connection straight-chain alkenyl residues with 2 to 12, especially with 2 to 7, carbon atoms in which the double bond is situated in the 1-position, such as, for example, vinyl, 1E-propenyl, 1E-butenyl, 1E-pentyl, 1E-hexenyl, 1E-heptenyl and the like.

The term "3E-alkenyl" preferably denotes in this connection straight-chain alkenyl residues with 4 to 12, especially with 4 to 7, carbon atoms in which the double bond is situated in the 3-position, such as, for example, 3-butenyl, 3E-pentenyl, 3E-hexenyl, 3E-heptenyl and the like.

The term "4-alkenyl" preferably denotes in this connection straight-chain alkenyl residues with 5 to 12 carbon atoms in which the double bond is situated in the 4-position, such as, for example, 4-pentenyl, 4-hexenyl, 4-heptenyl and the like.

The term "2E- or 3Z-alkenyloxy" preferably denotes in this connection straight-chain alkenyloxy residues with 3 or 4 to 12 carbon atoms, especially with 3 or 4 to 7 carbon atoms, in which the double bond is situated in the 2- or 3-position and E or R indicates the preferred configuration, such as, for example, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy and the like.

The term "1-alkynyl" preferably denotes in this connection straight-chain alkynyl residues with 2 to 12, especially with 2 to 7, carbon atoms in which the triple bond is situated in the 1-position, such as, for example, ethynyl, 1-propynyl, 1-butynyl, 1-pentynyl and the like.

The manufacture of the liquid crystalline mixtures and of the electro-optical devices can be effected in a known manner.

The invention is illustrated in more detail by the following Examples. In connection with liquid crystal phases and phase transitions C signifies a crystalline phase, SB signifies a smectic B phase, N signifies a nematic phase, N* signifies a cholesteric phase and I signifies the isotropic phase. The helical pitch is denoted by p and the wavelength of the selectively reflected, circular polarized light is denoted by $1_{max}$. Optical antipodes have in each case "mirror image properties", that is, the same melting points etc., but lead to opposite helical direction of rotation and opposite circular polarization of the reflected light.

EXAMPLE 1 a) 18.8 ml of butyllithium in hexane were added dropwise under nitrogen at −50° C. to 4 ml of ethynyltrimethylsilane in 50 ml of anhydrous tetrahydrofuran and after 30 minutes 57 ml of 1M ethereal zinc chloride solution were added dropwise. Thereupon, the cooling was removed and the mixture was left to react for 1 hr. Then, the reaction solution was cooled to 0° C. and 5 g of 4-(trans-4-propylcyclohexyl)phenyl trifluoromethylsulfonate in 50 ml of dimethylformamide, 0.824 g of tetrakis-(triphenylphosphine) palladium(O) and 1.2 g of lithium chloride were added in succession. The reaction mixture was heated to 85° C. and left to react at this temperature overnight. In order to complete the reaction an equal amount of the zinc ethynyltrimethylsilane solution, prepared as above, was thereupon added and the mixture was left to react at 85° C. After one hour it was cooled, treated with 20 ml of water, partitioned between 1N sulphuric acid and pentane and the separated organic phase was washed with water. The organic phase was dried over magnesium sulphate, filtered over Celite and evaporated completely. This gave 3.82 g of 1[-4-(trans-4-propylcyclohexyl)phenyl]-2-trimethylsilylacetylene as a solid mass (GC purity 97%), which was used directly in the next step.

b) A mixture of 3.8 g of 1[-4-(trans-4-propylcyclohexyl)phenyl]-2-trimethylsilylacetylene, 0.4 g of potassium carbonate and 50 ml of methanol/ether (2:1) was stirred at room temperature for 1 hr. Then, the mixture was partitioned between water and ether and the organic phase was washed in succession with saturated sodium chloride solution and water, dried over magnesium sulfate, filtered over Celite and evaporated. After chromatography of the residue over 150 silica gel with cyclohexane 1.95 g of 4-(trans-4-propylcyclohexyl)phenylacetylene were obtained as a colourless solid.

c) 0.54 ml of boron trifluoride etherate was added dropwise at 0° C. to a solution of 5 g of 4-bromobenzaldehyde and 13.2 g of dibutyl (2R,3R)-2,3-bis-trimethylsilyloxyglutarate and then the mixture was left to react for 30 minutes. Thereafter, 0.24 ml of trifluoromethanesulfonic acid was added at 0° C. and the mixture was left to react for 30 minutes. Then, the cooling bath was removed and the reaction mixture was stirred at room temperature for 4 hours. Subsequently, the reaction solution was poured into a saturated aqueous sodium bicarbonate solution, partitioned between water and methylene chloride and the organic phase was separated, dried over magnesium sulfate, filtered over Celite and evaporated. Chromatography of the residue on 250 g of silica gel with ethyl acetate/cyclohexane (1:9) gave 9.3 g of dibutyl (4R,5R)-2-(4-bromophenyl)- 1,3-dioxolane-4,5-dicarboxylate (GC purity 98%).

d) 1.45 ml of an about 1.6M butyllithium solution in hexane were added dropwise at −50° C. to a solution of 0.5 g of 4-(trans-4-propylcyclohexyl)phenylacetylene in 5 ml of dry tetrahydrofuran and the mixture was left to react at this temperature for 30 min. Then, 4.4 ml of a 1M zinc chloride solution in ether were added dropwise, the cooling bath was removed and the mixture was left to react for 30 minutes. Thereupon, the mixture was cooled to 0° C. and at this temperature a solution of 0.95 g of dibutyl (4R,5R)-2-(4-bromophenyl)-1,3-dioxolane-4,5-dicarboxylate in 5 ml of dry tetrahydrofuran was added dropwise and thereafter 0.128 g of tetrakis(triphenylphosphine) palladium(O) was added. The reaction mixture was then heated to 60° C. for 15 hours., then cooled, partitioned between water and ether and the organic phase was separated and dried over magnesium sulfate. Thereupon, it was filtered over Celite, the solvent was evaporated and the residue was chromatographed on 100 g of silica gel with 5% ethyl acetate in cyclohexane. Further purification with active charcoal in isopropanol and two-fold crystallization from isopropanol gave 0.23 g of dibutyl (4R,5R)-2-{4-[4-(trans-4-propylcyclohexyl)phenylethynyl]phenyl}- 1,3-dioxolane-4,5-dicarboxylate, m.p. (K-N*) 74.9° C., cl.p. (N*-I) 78.3° C.

The following compounds can be prepared in an analogous manner:

Diethyl (4R,5R)-2-{4-[4-(trans-4-propylcyclohexyl)phenylethynyl]phenyl}- 1,3-dioxolane-4,5-dicarboxylate;

dibutyl (4R,5R)-2-{4-[4-(trans-4-pentylcyclohexyl)phenylethynyl]phenyl}- 1,3-dioxolane-4,5-dicarboxylate;

dibutyl (4R,5R)-2-{4-[2,3-difluoro-4-(trans-4-propylcyclohexyl)phenylethynyl]phenyl}- 1,3-dioxolane-4,5-dicarboxylate;

dibutyl (4R,5R)-2-{2,3-difluoro-4-[4-(trans-4-propylcyclohexyl)phenylethynyl]phenyl}- 1,3-dioxolane-4,5-dicarboxylate; m.p. (K-I) 73.4° C., cl.p. (N*-I) 68.2° C.;

dibutyl (4R,5R)-2-{3-fluoro-4-[2-fluoro-4-(trans-4 -propylcyclohexyl)phenylethynyl]phenyl}-1,3-dioxolane-4,5-dicarboxylate;

dibutyl (4R,5R)-2-[4-(4-propyl-phenylethynyl)phenyl]-1,3 -dioxolane-4,5-dicarboxylate;

dibutyl (4R,5R)-2-{4-[4-(2,3-difluoro-4-propylphenyl)phenylethynyl]phenyl}- 1,3-dioxolane-4,5-dicarboxylate;

dibutyl (4R,5R)-2-{4-[4-(2,3-difluoro-4-pentylphenyl)phenylethynyl]phenyl}- 1,3-dioxolane-4,5-dicarboxylate;

dibutyl (4R,5R)-2-{4-[2,3-difluoro-4-(4-propylphenyl)phenylethinyl]phenyl}- 1,3-dioxolane-4,5-dicarboxylate;

dibutyl (4R,5R)-2-{4-[4-(2,3-difluoro-4-propyloxyphenyl)phenylethynyl]phenyl}- 1,3-dioxolane-4,5-dicarboxylate;

dibutyl (4R,5R)-2-[4-(2,3-difluoro-4-propyl-phenylethynyl)phenyl]- 1,3-dioxolane-4,5-dicarboxylate m.p. (K-I) 35° C.;

dibutyl (4R,5R)-2-[2,3-difluoro-4-(4-propyl-phenylethynyl)phenyl]- 1,3-dioxolane-4,5-dicarboxylate m.p. (K-I) 75.3° C.;

dibutyl (4R,5R)-2-[3-fluoro-4-(2-fluoro-4-propyl-phenylethynyl)phenyl]- 1,3-dioxolane-4,5-dicarboxylate;

dibutyl (4R,5R)-2-[4-(2,3-difluoro-4-pentyl-phenylethynyl)phenyl]- 1,3-dioxolane-4,5-dicarboxylate;

diethyl (4R,5R)-2-[4-(2,3-difluoro-4-pentyl-phenylethynyl)phenyl]- 1,3-dioxolane-4,5-dicarboxylate;

dibutyl (4R,5R)-2-{4-[4-(2-(trans-4-propylcyclohexyl)ethyl)phenylethynyl]phenyl}- 1,3-dioxolane-4,5-dicarboxylate;

dibutyl (4R,5R)-2-{4-[2,3-difluoro-4-(2-(trans-4 -propylcyclohexyl)ethyl)phenylethynyl]phenyl}-1,3-dioxolane-4,5-dicarboxylate;

EXAMPLE 2 a) A mixture of 1 g of 4-ethynyl-benzaldehyde, 1.56 g of 4-bromobenzaldehyde, 0.22 g of tetrakis(triphenylphosphine)-palladium(O) and 10 ml of triethylamine was stirred at 80° C. for 16 hours. Then, the reaction mixture was partitioned between water and methylene chloride and the organic phase was separated, dried over magnesium sulfate, filtered and evaporated. This gave 1.54 g of tolane-4,4'-dicarboxaldehyde as a solid brownish residue (GC purity 98.8%), which was used without further purification for the following step.

b) A suspension of 0.5 g of tolane-4,4'-dicarboxaldehyde in 5 ml of methylene chloride was added to a mixture of 2.6 g of dibutyl (2R,3R)-2,3-bis-trimethylsilyloxy-glutarate, 0,039ml of trimethylsilyl trifluoromethanesulfonate and 10 ml of methylene chloride and the reaction mixture was stirred at room temperature for 4 hours. Thereupon, a further 0.04 ml of trimethylsilyl trifluoromethanesulfonate was added and the mixture was stirred at room temperature for a further 64 hours. After adding 0.5 ml of pyridine the reaction mixture was partitioned between sodium bicarbonate and methylene chloride and the organic phase was separated, dried over magnesium sulfate, filtered over a mixture of Celite/Alox (neutral, act. III) and evaporated. Chromatography of the residue on 100 g of silica gel with 5% ethyl acetate in toluene and subsequent crystallization from hexane and then from isopropanol gave 0.88 g of 4,4'-bis-[(4R,5R)-4,5-dibutyloxycarbonyl- 1,3-dioxolan-2-yl]tolane as white crystals, m.p. 54° C.

The following compounds can be prepared in an analogous manner:

4,4'-Bis-[(4R,5R)-4,5-diethoxycarbonyl-1,3-dioxolan-2-yl]tolane;

4,4'-bis-[(4R,5R)-4,5-dimethoxycarbonyl-1,3-dioxolan-2-yl]tolane;

2,3-difluoro-4,4'-bis-[(4R,5R)-4,5-dibutyloxycarbonyl-1,3-dioxolan-2-yl]tolane;

2,2'-difluoro-4,4'-bis-[(4R,5R)-4,5-dibutyloxycarbonyl-1,3-dioxolan-2-yl]tolane, m.p. (K-I) 70° C., cl.p. monotropic (S*-I) 59.8° C.;

4-{4-[(4R,5R)-4,5-diethoxycarbonyl-1,3-dioxolan-2-yl]phenyl}- 4'-[(4R,5R)-4,5-dibutyloxycarbonyl-1,3-dioxolan-2-yl]tolane;

4-{2,3-difluoro-4-[(4R,5R)-4,5-diethoxycarbonyl-1,3-dioxolan- 2-yl]phenyl}-4'-[(4R,5R)-4,5-dibutyloxycarbonyl-1,3-dioxolan-2-yl]tolane;

2,3-difluoro-4-[4-[(4R,5R)-4,5-dibutyloxycarbonyl-1,3-dioxolan- 2-yl]phenyl]-4'-[(4R,5R)-4,5-dibutyloxycarbonyl-1,3 -dioxolan-2-yl]tolane, m.p. (K-I) 73.1° C.

4-[4-[(4R,5R)-4,5-diethoxycarbonyl-1,3-dioxolan-2-yl]phenyl}- 2',3'-difluoro-4'-[(4R,5R)-4,5-dibutyloxycarbonyl-1,3-dioxolan-2-yl]tolane;

EXAMPLE 3

The following liquid crystal basic mixture BM-1 was used to measure the induced pitch and its temperature dependence in liquid crystal materials:

| | |
|---|---|
| 5.36 wt. % of | 4'-ethyl-4-cyanobiphenyl, |
| 3.8 wt. % of | 4'-propyl-4-cyanobiphenyl, |
| 6.08 wt. % of | 4'-butyl-4-cyanobiphenyl, |
| 6.53 wt. % of | 4-(trans-4-propylcyclohexyl)benzonitrile, |
| 14.64 wt. % of | 4-(trans-4-pentylcyclohexyl)benzonitrile, |
| 5.21 wt. % of | 4-ethyl-1-(trans-4-propylcyclohexyl)benzene, |
| 16.54 wt. % of | 4-ethoxy-1-[2-(trans-e-propylcyclohexyl)ethyl]benzene, |
| 5.60 wt. % of | 4"-pentyl-4-cyano-p-terphenyl, |
| 5.71 wt. % of | 4'-(trans-4-pentylcyclohexyl)-4-cyanobiphenyl, |
| 15.59 wt. % of | 1-[2-trans-4-butylcyclohexyl)ethyl]-4-(trans-4-pentylcyclohexyl)benzene, |
| 4.74 wt. % of | 1-[2-trans-4-butylcyclohexyl)ethyl]-4'-(trans-4-pentylcyclohexyl)biphenyl, |
| 7.59 wt. % of | 1-[2-trans-4-butylcyclohexyl)ethyl]-4'-(trans-4-pentylcyclohexyl)-1,1'-ethylenedibenzene, |
| 2.84 wt. % of | 1-[2-trans-4-propylcyclohexyl)ethyl]-cyclohexanecarboxylic acid 4-cyanophenyl ester. |

Liquid crystal basic mixture BM-1 was treated with 1.0 wt. % of each of the following optically active dopants:

| | |
|---|---|
| D-1 = | dibutyl 4R,5R)-2-{4-[4-(trans-4-propylcyclohexyl)-phenylethynyl]phenyl}-1,3-dioxolane-4,5-dicarboxylate, |
| D-2 = | dibutyl (4R,5R)-2-{2,3-difluoro-4-[4-(trans-4-propylcyclohexyl)phenylethynyl]phenyl}-1,3-dioxolane-4,5-dicarboxylate, |
| D-3 = | dibutyl (4R,5R)-2-[4-(2,3-difluoro-4-propylphenylethynyl)phenyl]-1,3-dioxolane-4,5-dicarboxylate, |
| D-4 = | dibutyl (4R,5R)-2-[2,3-difluoro-4-(4-propylphenylethynyl)phenyl]-1,3-dioxolane-4,5-dicarboxylate, |
| D-5 = | 4,4'-bis-[(4R,5R)-4,5-dibutyloxycarbonyl-1,3-dioxolan-2-yl]tolane, |
| D-6 = | 4,4'-bis-[(4S,5S)-4,5-dibutyloxycarbonyl-1,3-dioxolan-2-yl]tolane, |
| D-7 = | 2,2'-difluoro-4,4'-bis-[(4R,5R)-4,5-dibutyloxycarbonyl-1,3-dioxolan-2-yl]tolane, |
| D-8 = | 2,3-difluoro-4-{4-[(4R,5R)-4,5-dibutyloxycarbonyl-1,3-dioxolan-2-yl]-phenyl}-4'-[(4R,5R)-4,5-dibutyloxycarbonyl-1,3-dioxolan-2-yl]tolane. |

The results compiled in Table 1 were obtained for the chiral doped mixtures, with A, B and C denoting the parameters of the equation $$\frac{1}{pc} = A + BT_1 + CT_1^2$$

and p, c and $T_1$ having the following significances:

| | |
|---|---|
| $T_1 =$ | T-22° C. |
| T = | temperature in °C. |
| p = | pitch in mm (a positive value signifies dextrorotating helical structure and a negative value signifies levorotating helical structure) |
| C = | concentration of the optically active dopant in wt. %. |

TABLE 1

| | Measured parameter of 1 wt. % of the respective dopant in the basic mixture BM-1 at 22° C. | | | |
|---|---|---|---|---|
| | A | B | C | |
| | [$10^{-2}$.mm$^{-1}$. | [$10^{-4}$.mm$^{-1}$. | [$10^{-6}$.mm$^{-1}$. | p.c (22° C.) |
| Dopant | wt. %$^{-1}$] | wt. %$^{-1}$] | wt. %$^{-1}$] | [mm.wt. %] |
| D-1 | −16.9 | 4.99 | −1.84 | −5.90 |
| D-2 | −10.5 | −0.77 | −0.61 | −9.50 |
| D-3 | −17.2 | 7.40 | −3.30 | −5.81 |
| D-4 | −11.9 | −0.34 | −1.51 | −8.38 |
| D-5 | −26.1 | 8.39 | −4.52 | −3.83 |
| D-6 | 25.7 | −7.93 | 2.77 | 3.89 |
| D-7 | −18.0 | 2.0 | −0.76 | −5.57 |
| D-8 | −22.1 | 2.70 | −0.70 | −4.53 |

We claim:

1. An optically active compound of the formula:

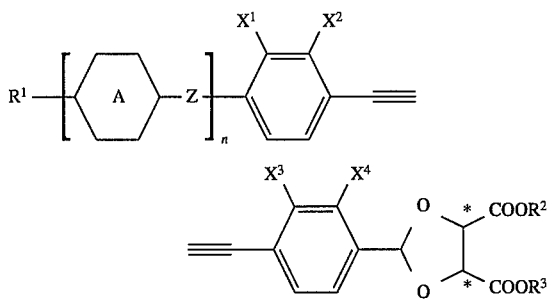

wherein ring A is 1,4-phenylene which is optionally substituted with one or more fluorine atoms, chlorine atoms, bromine atoms, cyano groups or methyl groups, and in which one or two CH groups can be replaced by nitrogen, or is trans-1,4-cyclohexylene;

Z is a single covalent bond, —CH$_2$CH$_2$—, —CH$_2$O— or —OCH$_2$—;

X$^1$,X$^2$,X$^3$,X$^4$ each independently are hydrogen or fluorine;

R$^1$ is hydrogen, is alkyl with 1 to 12 carbon atoms which is optionally substituted with one or more fluorine or chlorine atoms and in which one or two non-adjacent CH$_2$ groups can be replaced by —O—, is alkenyl with 2 to 12 carbon atoms which is optionally substituted with one or more fluorine or chlorine atoms and in which one or two non-adjacent CH$_2$ groups can be replaced by —O—, and when R$^1$ is bonded to an aromatic ring, can also be fluorine, chlorine, cyano, CF$_3$, OCHF$_2$ or —OCF$_3$;

R$^2$,R$^3$,R$^4$,R$^5$ are alkyl with 1 to 8 carbon atoms or alkenyl with 2 to 8 carbon atoms;

n is 0 or 1; and

* is a center of chirality.

2. An optically active compound according to claim 1, wherein the centers of chirality in the 4-position and 5-position of the dioxolane ring both have the [R] configuration or both have the [S] configuration.

3. An optically active compound according to claim 1, wherein n=1.

4. An optically active compound according to claim 1, wherein X$^1$ and X$^2$ or X$^3$ and X$^4$ are fluorine.

5. An optically active compound according to claims 1, wherein R$^1$ is alkyl or alkoxy with 1 to 6 carbon atoms or is alkenyl, alkenyloxy, or alkoxyalkyl with 2 to 6 carbon atoms or is alkoxyalkenyl with 3 to 6 carbon atoms.

6. An optically active compound of the formula

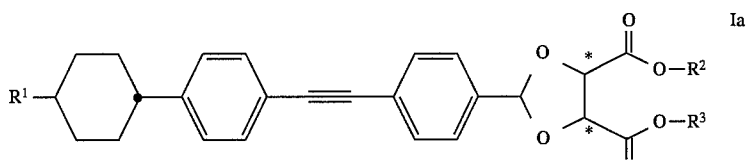

Ia

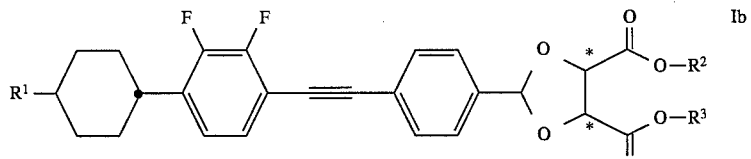

Ib

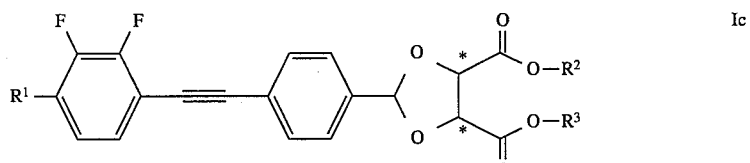

Ic

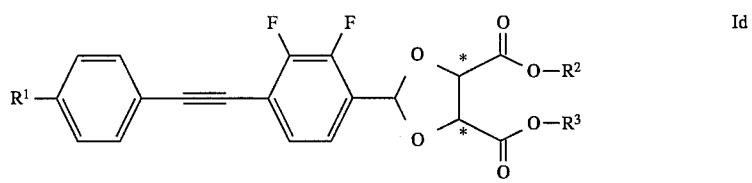

Id

-continued

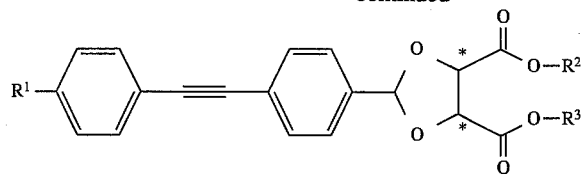

Ie wherein R¹ is hydrogen, is alkyl with 1 to 12 carbon atoms which is optionally substituted with one or more fluorine or chlorine atoms and in which one —CH₂— group can be replaced by —O—, is alkenyl with 2 to 12 carbons which is optionally substituted with one or more fluorine or chlorine atoms and in which one —CH₂— group can be replaced by —O—, and when R¹ is bonded to an aromatic ring, can also be fluorine, chlorine, cyano, CF₃, —OCHF₂ or —OCF₃; and R² and R³ are alkyl with 1 to 8 carbon atoms or alkenyl with 2 to 8 carbon atoms.

7. A liquid crystalline mixture containing a liquid crystalline carrier material and at least one optically active compound

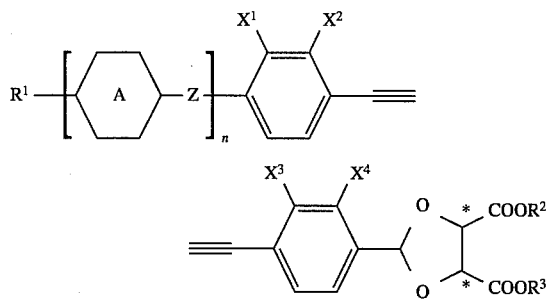

I wherein ring A is 1,4-phenylene which is optionally substituted with one or more fluorine atoms, chlorine atoms, bromine atoms, cyano groups or methyl groups, and in which one or two CH groups can be replaced by nitrogen, or is trans-1,4-cyclohexylene;

Z is a single covalent bond, —CH₂CH₂—, —CH₂O— or —OCH₂—;

X¹,X²,X³,X⁴ each independently are hydrogen or fluorine;

R¹ is hydrogen, is alkyl with 1 to 12 carbon atoms which is optionally substituted with one or more fluorine or chlorine atoms and in which one or two non-adjacent CH₂ groups can be replaced by —O—, is alkenyl with 2 to 12 carbon atoms which is optionally substituted with one or more fluorine or chlorine atoms and in which one or two non-adjacent CH₂ groups can be replaced by —O—, and when R¹ is bonded to an aromatic ring, can also be fluorine, chlorine, cyano, CF₂, OCHF₂ or —OCF₃;

R²,R³,R⁴,R⁵ are alkyl with 1 to 8 carbon atoms or alkenyl with 2 to 8 carbon atoms;

n is 0 or 1; and

* is a center of chirality.

8. A liquid crystalline mixture according to claim 7, wherein the content of compounds of formula I is about 0.1–30 wt. %.

* * * * *

UNITED STATES PATENT AND TRADEMARK OFFICE
CERTIFICATE OF CORRECTION

PATENT NO. : 5,498,367
DATED : March 12, 1996
INVENTOR(S) : Buchecker, et al.

It is certified that error appears in the above-indentified patent and that said Letters Patent is hereby corrected as shown below:

Title Page, item [57] left side
lines 1-5;

Column 1, lines 60-65 and continuing to Column 2, lines 1-5;

Column 2, lines 40-50;

Claim 1, Column 19, lines 20-30;

Claim 7, Column 21, lines 25-35.

In each instance formula I reads:

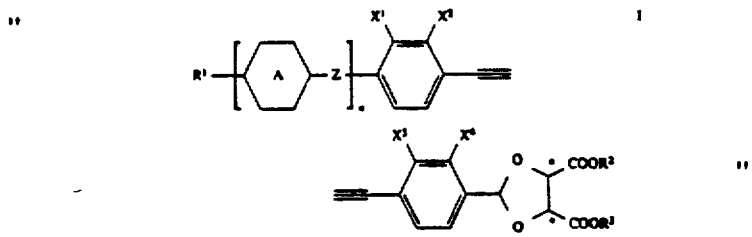

UNITED STATES PATENT AND TRADEMARK OFFICE
CERTIFICATE OF CORRECTION

PATENT NO. : 5,498,367
DATED : March 12, 1996
INVENTOR(S) : Buchecker, et al.

It is certified that error appears in the above-indentified patent and that said Letters Patent is hereby corrected as shown below:

In each instance formula I should read

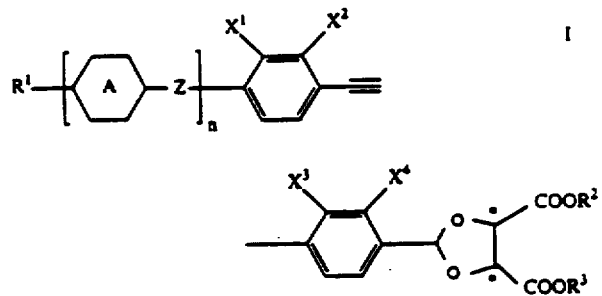

Signed and Sealed this

Eleventh Day of February, 1997

Attest:

BRUCE LEHMAN

Attesting Officer    Commissioner of Patents and Trademarks